(12) United States Patent
Ishimaru et al.

(10) Patent No.: US 8,192,996 B2
(45) Date of Patent: Jun. 5, 2012

(54) METHOD FOR STORING TETRAZOLIUM COMPOUND, STABILIZER USED IN THE SAME, AND TETRAZOLIUM COMPOUND REAGENT SOLUTION USING THE METHOD

(75) Inventors: Kaori Ishimaru, Kyoto (JP); Satoshi Yonehara, Kyoto (JP)

(73) Assignee: Arkray, Inc., Kyoto (JP)

( * ) Notice: Subject to any disclaimer, the term of this patent is extended or adjusted under 35 U.S.C. 154(b) by 446 days.

(21) Appl. No.: 12/416,507

(22) Filed: Apr. 1, 2009

(65) Prior Publication Data

US 2009/0215026 A1 Aug. 27, 2009

Related U.S. Application Data

(62) Division of application No. 10/478,785, filed as application No. PCT/JP02/09889 on Sep. 25, 2002, now abandoned.

(30) Foreign Application Priority Data

Sep. 28, 2001 (JP) .................... 2001-302556

(51) Int. Cl.
*G01N 33/72* (2006.01)
*G01N 33/00* (2006.01)
*G01N 21/00* (2006.01)
*G01N 21/75* (2006.01)

(52) U.S. Cl. ............ 436/67; 436/87; 436/164; 436/166
(58) Field of Classification Search ............ 436/67, 436/87, 164, 166
See application file for complete search history.

(56) References Cited

U.S. PATENT DOCUMENTS

| 3,703,591 A | 11/1972 | Bucolo |
| 3,884,764 A * | 5/1975 | Goodhue et al. ............. 435/11 |
| 4,061,468 A | 12/1977 | Lange et al. |
| 4,195,126 A | 3/1980 | Hall |
| 4,259,440 A | 3/1981 | Gupta et al. |
| 4,748,115 A | 5/1988 | Steaffens |
| 5,196,314 A | 3/1993 | Town et al. |
| 6,790,665 B2 * | 9/2004 | Yonehara et al. ............. 436/66 |

FOREIGN PATENT DOCUMENTS

| EP | 1 002 874 | 11/1999 |
| JP | 61-241743 | 10/1986 |
| WO | WO 02/27330 | * 4/2002 |

OTHER PUBLICATIONS

Serva GmbH "Tetrazolium Salts—highly sensitive colout indicators of enzymatic redox reactions" Available May 24, 2001, www.serva.de/products/lastest/tetrazolium, Accessed May 18, 2006.
Dojindo Molecular Technologies "Product Name: WST-3" www.dojindo.com/products/keyword/dojindodtll.cfm, 8 pages Accessed May 18, 2006.
Robert J. Kadner, Joseph F. NYC "A Repressible Alkaline Phosphatase in Neurospora crassa" The Journal of Biological Chemistry, vol. 244, No. 19, Issue of Oct. 10, pp. 5125-5130, 1969.
Jones, Gareth E. Human Cell Culture Protocols, Humana Press 1996, p. 103.

* cited by examiner

*Primary Examiner* — Jon P Weber
*Assistant Examiner* — Thane Underdahl
(74) *Attorney, Agent, or Firm* — Morgan, Lewis & Bockius LLP

(57) ABSTRACT

A method for storing a tetrazolium compound stably is provided. The tetrazolium compound is stored in the presence of sodium azide. The tetrazolium compound (A) and the sodium azide (B) are present at a ratio (A:B) in the range from 1:0.02 to 1:6.2. Furthermore, when the tetrazolium compound is stored as a solution, the concentration of the sodium azide is in the range from 0.08 to 3.2 mmol/L and the concentration of the tetrazolium compound is in the range from 0.5 to 8 mmol/L. As the tetrazolium compound, it is preferable to use 2-(4-iodophenyl)-3-(2,4-dinitrophenyl)-5-(2,4-disulfophenyl)-2H-tetrazolium salt.

5 Claims, 3 Drawing Sheets

METHOD FOR STORING TETRAZOLIUM COMPOUND, STABILIZER USED IN THE SAME, AND TETRAZOLIUM COMPOUND REAGENT SOLUTION USING THE METHOD

CROSS-REFERENCE TO RELATED APPLICATIONS

This application is a Division of application Ser. No. 10/478,785, filed Nov. 24, 2003, which is a U.S. National Stage application of International Application No. PCT/JP02/09889, filed Sep. 25, 2002, which applications are incorporated herein by reference.

TECHNICAL FIELD

The present invention relates to a method for storing a tetrazolium compound stably, a stabilizer used in the method, and a tetrazolium compound reagent solution using the method.

BACKGROUND ART

Tetrazolium compounds generally are used as a redox dye (a color-developing substrate), a reducing agent, or the like. To this end, a liquid reagent prepared by dissolving a tetrazolium compound in water usually is used.

However, in the case where the pH of the tetrazolium compound solution is close to neutral, the tetrazolium compound exhibits low stability. Thus, when the tetrazolium compound solution is stored for a long time, there arises a problem in that the solution may be colored due to spontaneous color development of the tetrazolium compound or that the solution may no longer act as a reducing agent, for example. On this account, when a tetrazolium compound solution needs to be used, there is no other way but to prepare a tetrazolium compound solution for each use or to use a tetrazolium compound solution stored as an acid solution because the tetrazolium compound is stable even in the form of a solution under acidic conditions.

DISCLOSURE OF INVENTION

However, in the case where a tetrazolium compound is used in an enzyme reaction system, it is necessary to set various conditions according to the reaction. In particular, enzymes have their own optimum pH and pH stability, and these optimum pH and pH stability are not necessarily acidic. In fact, the optimum pH and pH stability of many enzymes are alkaline, and in particular, there are a large number of enzymes whose optimum pH and pH stability are close to neutral. Thus, in the case where an enzyme reaction is caused at a pH close to neutral, if an acid solution containing a tetrazolium compound is to be used, it is necessary to adjust the pH of the reaction system when using the solution. This makes the operation complicated.

Therefore, it is an object of the present invention to provide a method for storing a tetrazolium compound stably not only under acidic conditions but also under other pH conditions.

In order to achieve the above object, the present invention provides a method for storing a tetrazolium compound stably, including: storing the tetrazolium compound in the presence of sodium azide. In the presence of the sodium azide, the tetrazolium compound can be stored in a stabilized condition where, for example, the spontaneous color development thereof is suppressed and the function thereof is maintained not only under acidic conditions but also under other pH conditions.

In the present invention, the tetrazolium compound may be stored in the form of a solution or in the dry state. In the case where the tetrazolium compound is stored in the dry state, the tetrazolium compound may be stored, for example, by adding sodium azide to a solution containing the tetrazolium compound and then drying this mixture as it is. Alternatively, filter paper or the like may be impregnated with this mixture and then dried.

The sodium azide generally is used as an antiseptic. However, in the present invention, the sodium azide is not added to produce an antiseptic effect but to store the tetrazolium compound in a stabilized condition where the spontaneous color development thereof is suppressed and the function thereof is maintained. It is the inventors of the present invention who discovered that sodium azide can stabilize a tetrazolium compound.

In the method according to the present invention, it is preferable that the tetrazolium compound (A) and the sodium azide (B) are present at a ratio (molar ratio A:B) in a range from 1:0.02 to 1:6.2.

In the method according to the present invention, when the tetrazolium compound and the sodium azide are present in a solution so that the tetrazolium compound is stored stably, it is preferable that a concentration of the sodium azide is in a range from 0.08 to 3.2 mmol/L, more preferably 0.08 to 0.8 mmol/L. This is because the tetrazolium compound can be stored even more stably when the concentration of the sodium azide is in the above-described range. On the other hand, when the sodium azide is used as an antiseptic as described above, the concentration of the sodium azide needs to be about 0.05 to 0.2 wt % (7.7 to 31 mol/L) in order to produce an antiseptic effect. However, in the present invention, the sodium azide exhibits a particularly excellent effect of stabilizing the tetrazolium compound when the concentration thereof is in the range from 0.08 to 3.2 mmol/L. Within this range, the sodium azide exhibits substantially no antiseptic effect. That is, it is considered that the stabilization of the tetrazolium compound is not achieved by the antiseptic effect of the sodium azide, and it can be said that the antiseptic effect and the effect of stabilizing the tetrazolium compound are completely different from each other.

On the other hand, in the method according to the present invention, it is preferable that a concentration of the tetrazolium compound is in a range from 0.5 to 8 mmol/L.

Furthermore, in the method according to the present invention, it is preferable that the sodium azide is added to the solution so that its concentration falls within the range from 0.02 to 6.2 mmol/L per 1 mmol/L of the tetrazolium compound.

In the method according to the present invention, a pH of the solution is not particularly limited, but is, for example, in the range from 5.0 to 7.5, preferably 5.0 to 7.0, and more preferably 5.5 to 6.5.

In the method according to the present invention, it is preferable that the tetrazolium compound is 2-(4-iodophenyl)-3-(2,4-dinitrophenyl)-5-(2,4-disulfophenyl)-2H-tetrazolium salt.

Next, a stabilizer according to the present invention is a stabilizer for storing a tetrazolium compound stably, which includes sodium azide. The reason for this is that the sodium azide can stabilize the tetrazolium compound as described above.

Next, a tetrazolium compound reagent according to the present invention is a reagent solution including an aqueous solvent and a tetrazolium compound dissolved in the aqueous solvent, and sodium azide further is dissolved in the aqueous solvent. In such a reagent, spontaneous color development of the tetrazolium compound or loss of the function of the tetrazolium compound can be suppressed even if the reagent is in the form of a solution. Therefore, the necessity of preparing a reagent solution for each use is eliminated so that operations using a tetrazolium compound, such as various measurement reactions, can be carried out simply.

Furthermore, a dry reagent according to the present invention is a tetrazolium compound-containing reagent obtained by drying an aqueous solvent in which the tetrazolium compound and sodium azide are dissolved. The aqueous solvent in which the tetrazolium compound and sodium azide are dissolved may be dried as it is. Alternatively, filter paper or the like may be impregnated with the aqueous solvent and then dried.

BRIEF DESCRIPTION OF DRAWINGS

FIGS. 3A and 3B are graphs showing the change in absorbance in a method for storing a tetrazolium compound stably according to another example of the present invention, wherein FIG. 3A shows the result with respect to a sample having a WST-3 concentration of 0.5 mmol/L and a sodium azide concentration of 0.05 g/L and FIG. 3B shows the result with respect to a sample having a WST-3 concentration of 2.0 mmol/L and a sodium azide concentration of 0.1 g/L.

BEST MODE FOR CARRYING OUT THE INVENTION

Figure 1:
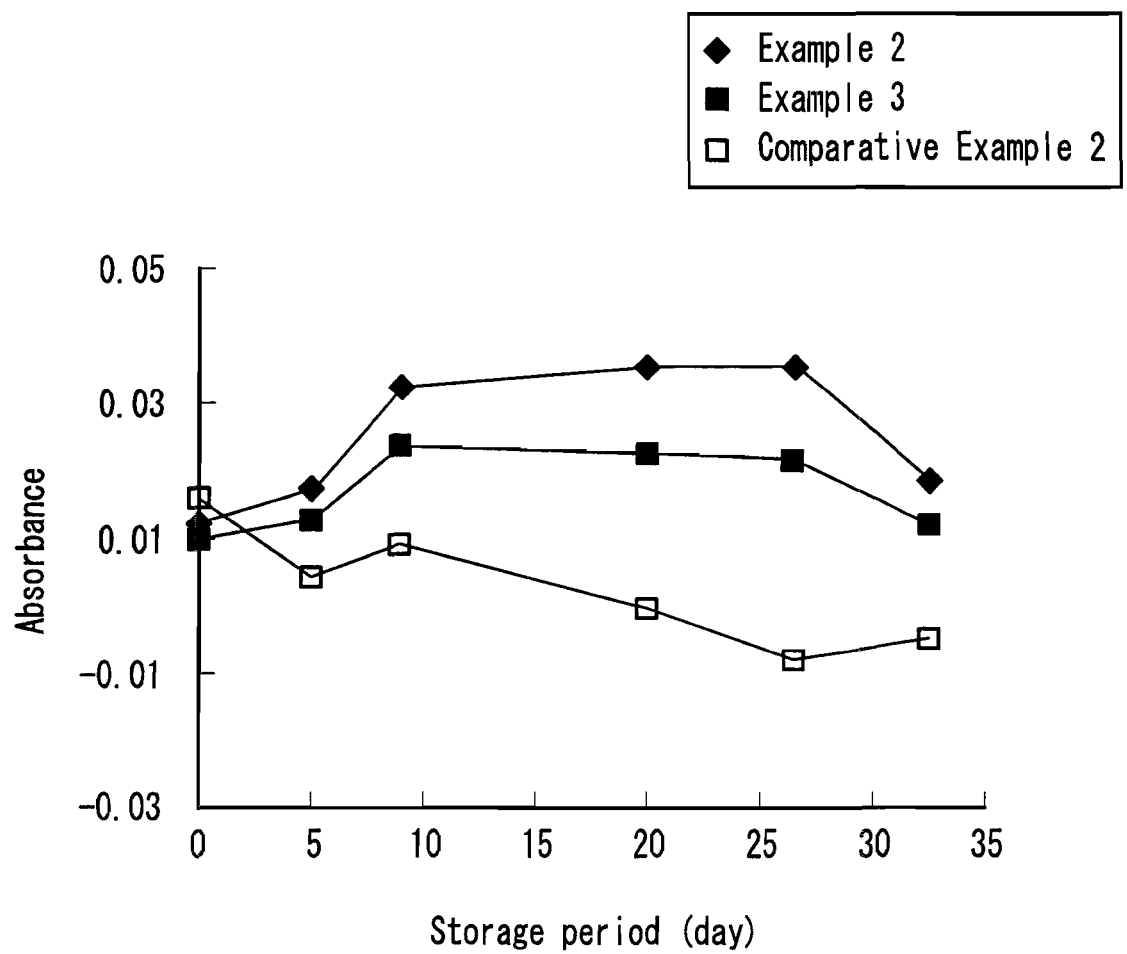
FIG. 1 is a graph showing the change in absorbance corresponding to an amount of glycated hemoglobin with time in a method for storing a tetrazolium compound stably according to one example of the present invention.

The tetrazolium compound to be used in a method for storing a tetrazolium compound stably according to the present invention preferably contains ring substituents at least at two positions on its tetrazole ring, more preferably at three positions on its tetrazole ring, for example.

In the case where the tetrazolium compound contains ring substituents at least at two positions on its tetrazole ring as described above, it is preferable that the ring substituents are at the 2-position and 3-position on the tetrazole ring. Further, in the case where the tetrazolium compound contains ring substituents at three positions on its tetrazole ring, it is preferable that the ring substituents are at the 2-position, 3-position, and 5-position on the tetrazole ring.

Further, it is preferable that at least two ring substituents of the tetrazolium compound have a benzene ring structure. Other than the benzene ring structure, the ring substituents may have a resonance structure with S or O being contained in the ring skeleton, for example. Examples of the ring substituents with such a resonance structure include a thienyl group, thiazoyl group, and the like.

Furthermore, it is preferable that the tetrazolium compound contains ring substituents at least at three positions on its tetrazole ring and at least two of the ring substituents have a benzene ring structure.

Still further, it is preferable that at least one ring substituent contains a functional group, and a larger number of functional groups are more preferable.

As the functional group, an electron-withdrawing functional group preferably is used. For example, a halogen group, ether group, ester group, carboxy group, acyl group, nitroso group, nitro group, hydroxy group, sulfo group, and the like can be used. Other than these, characteristic groups containing oxygen such as a hydroperoxy group, oxy group, epoxy group, epidioxy group, oxo group, and the like; and characteristic groups containing sulfur such as a mercapto group, alkylthio group, methylthiomethyl group, thioxo group, sulfino group, benzenesulfonyl group, phenylsulfonyl group, p-toluenesulfonyl group, p-tolylsulfonyl group, tosyl group, sulfamoyl group, isothiocyanate group, and the like also can be used, for example. Among these electron-withdrawing functional groups, a nitro group, sulfo group, halogen group, carboxy group, hydroxy group, methoxy group, ethoxy group are preferable. Further, in addition to the above-mentioned electron-withdrawing functional groups, unsaturated hydrocarbon groups such as a phenyl group ($C_6H_5$—), styryl group ($C_6H_5CH$=$CH$—), and the like also can be used, for example. It is to be noted that the functional groups may have been ionized by dissociation.

Still further, it is preferable that the tetrazolium compound contains benzene rings at the 2-position and 3-position on its tetrazole ring and at least one of the benzene rings contains at least one functional group selected from the group consisting of a halogen group, carboxy group, nitro group, hydroxy group, sulfo group, methoxy group, and ethoxy group. It is to be noted here that both the benzene rings may contain the functional group. Further, the functional group may be contained at any positions (ortho-, meta-, para-) on the benzene ring. Furthermore, the number of the functional group is not specifically limited, and the benzene ring may have either the same or different functional groups.

Examples of the tetrazolium compound containing ring substituents having a benzene ring structure at the 2-position, 3-position, and 5-position on its tetrazole ring include:

2-(4-iodophenyl)-3-(4-nitrophenyl)-5-(2,4-disulfophenyl)-2H-tetrazolium salt;
2-(4-iodophenyl)-3-(2,4-dinitrophenyl)-5-(2,4-disulfophenyl)-2H-tetrazolium salt;
2-(2-methoxy-4-nitrophenyl)-3-(4-nitrophenyl)-5-(2,4-disulfophenyl)-2H-tetrazolium salt;
2-(4-iodophenyl)-3-(4-nitrophenyl)-5-phenyl-2H-tetrazolium salt;
3,3'-(1,1'-biphenyl-4,4'-diyl)-bis(2,5-diphenyl)-2H-tetrazolium salt;
3,3'-[3,3'-dimethoxy-(1,1'-biphenyl)-4,4'-diyl]-bis[2-(4-nitrophenyl)-5-phenyl-2H-tetrazolium salt];
2,3-diphenyl-5-(4-chlorophenyl) tetrazolium salt;
2,5-diphenyl-3-(p-diphenyl) tetrazolium salt;
2,3-diphenyl-5-(p-diphenyl) tetrazolium salt;
2,5-diphenyl-3-(4-styrylphenyl) tetrazolium salt;
2,5-diphenyl-3-(m-tolyl) tetrazolium salt; and
2,5-diphenyl-3-(p-tolyl) tetrazolium salt.

The tetrazolium compound is not limited to those described above. In addition to the above-mentioned tetrazolium compounds, a tetrazolium compound containing ring substituents having a benzene ring structure at two positions and one ring substituent having a structure other than the benzene ring structure at one position on its tetrazole ring also may be used. Examples of such a tetrazolium compound include:

2,3-diphenyl-5-(2-thienyl) tetrazolium salt;
2-benzothiazoyl-3-(4-carboxy-2-methoxyphenyl)-5-[4-(2-sulfoethyl carbamoyl) phenyl]-2H-tetrazolium salt;

2,2'-dibenzothiazoyl-5,5'-bis[4-di(2-sulfoethyl)carbamoylphenyl]-3,3'-(3,3'-dimethoxy-4,4'-biphenylene)ditetrazolium salt; and 3-(4,5-dimethyl-2-thiazoyl)-2,5-diphenyl-2H-tetrazolium salt.

Further, a tetrazolium compound containing ring substituents having a benzene ring structure at two positions and one substituent not having a ring structure at one position on its tetrazole ring also can be used. Examples of such a tetrazolium compound include:

2,3-diphenyl-5-cyano tetrazolium salt;
2,3-diphenyl-5-carboxy tetrazolium salt;
2,3-diphenyl-5-methyltetrazolium salt; and
2,3-diphenyl-5-ethyl tetrazolium salt.

Among the above-mentioned tetrazolium compounds, the tetrazolium compounds containing three ring substituents are preferable as described above. Among these, the tetrazolium compounds containing three ring substituents having a benzene ring structure and a large number of electron-withdrawing functional groups is more preferable, and 2-(4-iodophenyl)-3-(2,4-dinitrophenyl)-5-(2,4-disulfophenyl)-2H-tetrazolium salt is most preferable. It is to be noted here that the above-mentioned tetrazolium compounds may be a salt or may have been ionized, for example.

The storage of a tetrazolium compound according to the present invention may be carried out, for example, by dissolving a tetrazolium compound and sodium azide as a stabilizer in an aqueous solvent and storing the thus-obtained tetrazolium compound aqueous solution. The concentration of the tetrazolium compound in the aqueous solution is not particularly limited, but is, for example, in the range from 0.5 to 8 mmol/L as described above, due to the solubility in water of the tetrazolium compound or the like.

On the other hand, the concentration of the sodium azide is, for example, in the range from 0.08 to 3.2 mmol/L, more preferably 0.08 to 0.8 mmol/L, as described above.

Furthermore, the sodium azide preferably is added to the solution so that its concentration falls within the range from 0.02 to 6.2 mmol/L per 1 mmol/L of the tetrazolium compound, for example.

As the aqueous solvent, water, various buffers, and the like can be used, for example. As the buffers, a phosphate buffer, Good's buffers (MES, MOPSO, MOPS, DIPSO, TES, POPSO, and HEPES), and the like can be used. Among these, MES and MOPS are preferable, and MES is more preferable. The pH of the buffer is, for example, in the range from 5.0 to 7.5, preferably 5.0 to 7.0, and more preferably 5.5 to 6.5.

In the presence of sodium azide, the tetrazolium compound can be stored stably without adjusting the pH of the aqueous solution so as to be acidic, as required conventionally. Thus, the pH of the aqueous solution is not particularly limited, but is, for example, in the range from 5.0 to 7.5, preferably 5.0 to 7.0, and more preferably 5.5 to 6.5.

The storage temperature of the aqueous solution containing the tetrazolium compound and the sodium azide is not particularly limited, but preferably is in the range from 4° C. to 60° C.

In the case where the aqueous solution is stored at 4° C., the aqueous solution can be stored for, for example, at least 90 days while suppressing spontaneous color development of the tetrazolium compound and maintaining the function of the tetrazolium compound.

The tetrazolium compound stored in the above-described manner is useful as a liquid tetrazolium compound reagent because spontaneous color development of the tetrazolium compound is suppressed and the function of the tetrazolium compound is maintained as described above even if the tetrazolium compound is stored as a solution for a long time. The application of the tetrazolium compound reagent is not particularly limited. For example, the tetrazolium compound reagent may be used as a color-developing substrate, a reducing agent, or the like as described above.

Furthermore, by drying the aqueous solution as it is or drying filter paper or the like impregnated with the aqueous solution as described above, the tetrazolium compound may be used as a dry reagent.

EXAMPLES

Example 1 and Comparative Example 1

In Example 1, a tetrazolium compound was stored as an aqueous solution in the presence of sodium azide, and the change in color in the aqueous solution was examined. As the tetrazolium compound, a product named "WST-3" (manufactured by Dojindo Laboratories, hereinafter the same) was used.

Samples having the following compositions were prepared by adding sodium azide so that the samples contained the sodium azide at predetermined concentrations (0.01, 0.03, 0.05, 0.07, 0.10, 0.20 g/L), respectively. These samples were stored at 40C.° for 8 days. After the storage, the absorbance of these samples at the wavelength of 450 nm was measured using a spectrophotometer (product name "Lambda 20", manufactured by PerkinElmer, Inc., hereinafter the same). The results are shown in Table 1 below. The sample containing no sodium azide (0 g/L) was regarded as Comparative Example 1.

| (Composition of Samples) | |
|---|---|
| PIPES buffer (pH 7.5) | 5 mmol/L |
| Tetrazolium compound | 0.5 mmol/L |
| Sodium azide | predetermined concentration |

TABLE 1

| Sodium azide (g/L) | 0 | 0.01 | 0.03 | 0.05 | 0.07 | 0.10 | 0.20 |
|---|---|---|---|---|---|---|---|
| Absorbance | 0.352 | 0.207 | 0.181 | 0.202 | 0.192 | 0.196 | 0.264 |

As shown in Table 1, in the presence of the sodium azide, the WST-3 could be stored stably with the color development of the WST-3 being suppressed even though the WST-3 was stored as an aqueous solution. Besides, even though the pH of the samples was close to neutral and not acidic as required conventionally, the WST-3 could be stored sufficiently stably. Furthermore, it can be said from the results that the amount of the sodium azide to be added preferably is in the range from 0.01 to 0.2 g/L per 0.5 mmol/L of the WST-3.

Example 2, Example 3, and Comparative Example 2

In these examples, a tetrazolium compound and a metalloproteinase were stored as an aqueous solution in the presence of sodium azide, and whether or not the aqueous solution was colored and whether or not the function of the tetrazolium compound was maintained were examined.

(Storage Procedure)

Enzyme reagents containing a tetrazolium compound were prepared so as to have the following compositions. These reagents were stored at predetermined temperatures (4° C. and 25° C.) and samples were taken from them at predetermined periods after the start of storage. With respect to the samples taken after the predetermined storage periods, whether or not the samples were colored was confirmed in the following manner. Further, measurement of glycated hemoglobin using each of these samples was carried out in the following manner. In Comparative Example 2, an enzyme reagent was prepared in the same manner as that in Examples 2 and 3 except that no sodium azide was added thereto, which was then stored and subjected to the confirmation of coloring and the measurement of glycated hemoglobin in the same manner as that in Examples 2 and 3. As the metalloproteinase shown below, a product named "Metalloproteinase" (Toyobo Co., Ltd.) was used.

(Composition of Tetrazolium Compound-Containing Enzyme Reagent)

|  |  | Ex. 1 | Ex. 2 | Com. Ex. 2 |
|---|---|---|---|---|
| Metalloproteinase | 2.0 g/L | ○ | ○ | ○ |
| WST-3 | 2.0 mmol/L | ○ | ○ | ○ |
| MOPS buffer (pH 6.5) | 5.0 mmol/L | ○ | — | — |
| MES buffer (pH 5.5) | 5.0 mmol/L | — | ○ | ○ |
| NaN$_3$ | 0.05 g/L | ○ | ○ | — |
| CaCl$_2$ | 1.0 mmol/L | ○ | ○ | ○ |
| NaCl | 300.0 mmol/L | ○ | ○ | ○ |

A. Method for Confirming Coloring

With respect to the enzyme reagent sample (storage period: 33 days), the absorbance (at the wavelength of 450 nm) was measured using the above-described spectrophotometer. The results are shown in Table 2.

TABLE 2

| Change in absorbance (unit: absorbance) | | | | | |
|---|---|---|---|---|---|
| Ex. 2 | | Ex. 3 | | Com. Ex. 2 | |
| 4° C. | 25° C. | 4° C. | 25° C. | 4° C. | 25° C. |
| 0.191 | 0.284 | 0.081 | 0.201 | 0.299 | 1.911 |

(33 days after preparation)

B. Measurement of Glycated Hemoglobin

In measurement of an analyte in a sample utilizing a redox reaction, when the sample contains a reducing substance such as ascorbic acid or hemoglobin, the measurement may not be carried out accurately because the reducing substance may reduce an oxide as the analyte, a color-developing substrate may develop color, or color developed may be disappeared, for example. In such cases, a tetrazolium compound is effective because it has a function of eliminating the influence of the reducing substance, such as hindrance to a reaction or color development error as described above, thereby improving the accuracy of the measurement. Therefore, by carrying out the measurement of glycated hemoglobin utilizing a redox reaction using a tetrazolium compound stored as an aqueous solution in the presence of sodium azide, it is possible to determine whether or not the tetrazolium compound still maintains its function after the storage.

In this measurement of glycated hemoglobin, the amount of the glycated hemoglobin is determined by degrading glycated hemoglobin with a protease; reacting a fructosyl amino acid oxidase (hereinafter, referred to as "FAOD") with a glycated side chain group of an amino acid residue in the degradation product so that hydrogen peroxide is generated; causing a redox reaction between the hydrogen peroxide and a color-developing substrate; and then measuring the color development of the substrate. Specific procedures for this measurement will be described in the following.

First, each measurement sample shown below was diluted 2-fold (by volume), and 25 µL of this diluted solution was mixed with 60 µL of each of the enzyme reagent samples taken after the storage for predetermined periods and 25 µL of a color-developing reagent shown below. The obtained mixtures (110 mL) were allowed to react for 15 minutes at 37° C. Thereafter, the absorbance of the mixtures at the main wavelength of 751 nm and the sub-wavelength of 805 nm was measured using a biochemical automatic analysis apparatus (product name "JCA-BM 8", manufactured by Japan Electron Optics Laboratory Co. Ltd.).

Figure 2:
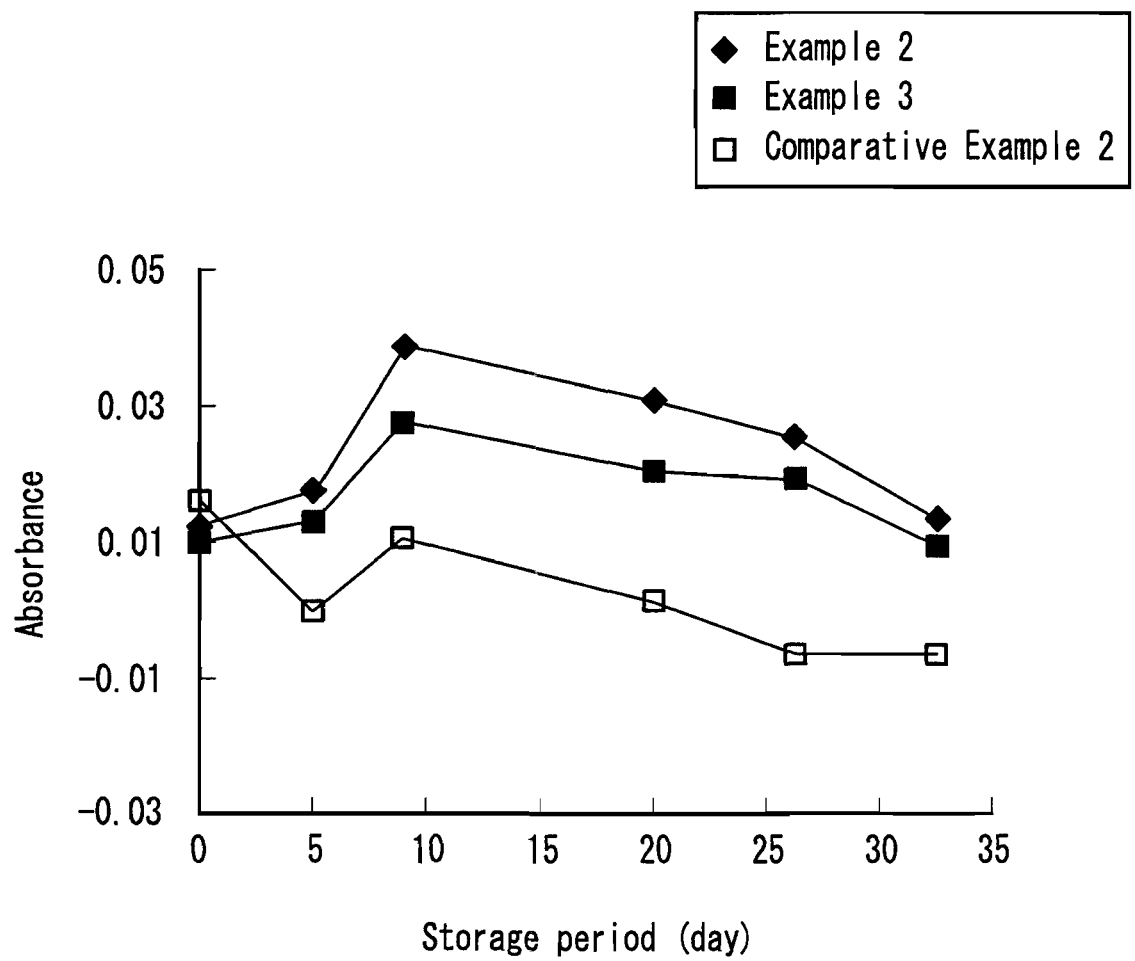
FIG. 2 is a graph showing the change in absorbance corresponding to an amount of glycated hemoglobin with time in the same example as in FIG. 1.

The results are shown in Tables 3 and 4 below and FIGS. 1 and 2. Table 3 and FIG. 1 show the result of the absorbance measurement in the case where the enzyme reagent samples containing the tetrazolium compound were stored at 4° C., and Table 4 and FIG. 2 show the result of the absorbance measurement in the case where the enzyme reagent samples containing the tetrazolium compound were stored at 25° C.

(Preparation of Measurement Sample)

The measurement samples were prepared so as to have the following compositions. The hemolysate sample shown below was prepared by freezing blood, storing it, and then melting it to hemolyze blood cells.

| Hemolysate sample (Hb concentration 100 g/L) | 50 µL, 150 µL, 250 µL |
|---|---|
| 20 wt % polyoxy lauryl ether | 84 µL |
| 1 mol/L glycinamide buffer (pH 9.0) | 81 µL |
| water | remaining portion |
| total amount | 750 µL |

(Composition of Color-Developing Reagent)

| FAOD | 26.0 KU/L |
|---|---|
| Peroxidase (POD) | 78.0 KU/L |
| Color-developing substrate | 0.052 mmol/L |
| Phosphate buffer (pH 6.9) | 0.20 mmol/L |

As the FAOD, a product named "Fructosyl Amino Acid Oxidase" (ARKRAY, INC.) was used. Furthermore, as the color-developing substrate, a product named "DA-64" (Wako Pure Chemical Industries, Ltd.) was used.

TABLE 3

Storage temperature: 4° C.

| | Absorbance | | |
|---|---|---|---|
| Storage period | Ex. 2 | Ex. 3 | Com. Ex. 2 |
| 0 day | 0.01159 | 0.00994 | 0.01652 |
| 5 days | 0.01797 | 0.01315 | 0.00480 |
| 9 days | 0.03295 | 0.02392 | 0.00967 |
| 20 days | 0.03591 | 0.02350 | 0.00058 |
| 26 days | 0.03502 | 0.02263 | −0.0081 |
| 33 days | 0.01934 | 0.01338 | −0.0033 |

TABLE 4

Storage temperature: 25° C.

| | Absorbance | | |
|---|---|---|---|
| Storage period | Ex. 2 | Ex. 3 | Com. Ex. 2 |
| 0 day | 0.01159 | 0.00994 | 0.01652 |
| 5 days | 0.01888 | 0.01335 | 0.00096 |
| 9 days | 0.04028 | 0.02840 | 0.01206 |
| 20 days | 0.03220 | 0.02172 | 0.00298 |
| 26 days | 0.02792 | 0.02076 | −0.0051 |
| 33 days | 0.01439 | 0.01125 | −0.0048 |

With regard to spontaneous color development of the tetrazolium compound in the case where the tetrazolium compound was stored as a solution, the color development was suppressed in Examples 2 and 3 far more strongly than in Comparative Example 2, as can be seen from Table 2. Furthermore, with regard to the glycated hemoglobin measurement, in Comparative Example 2, the absorbance decreased with time, which means that the tetrazolium compound gradually lost its function of eliminating the influence of the reducing substance. In contrast, in Examples 2 and 3, the absorbance after 30-day storage was substantially the same as that after O-day storage, which means that the function of the tetrazolium compound was maintained stably. Still further, with regard to storage conditions, it was found that the tetrazolium compound exhibits higher stability at pH 6.5, which is close to neutral, than at pH 5.5. Furthermore, as can be seen from FIGS. 1 and 2, in Examples 2 and 3, an increase in absorbance was observed, and particularly high absorbance was maintained 10 to 26 days after the start of the storage. From this fact, it can be said that, when a tetrazolium compound is stored as a solution in the presence of sodium azide, the tetrazolium compound can be stabilized and besides, the sensitivity of the measurement can be improved.

Example 4 and Comparative Example 3

In Example 4, a tetrazolium compound was stored as an aqueous solution having a predetermined pH in the presence of sodium azide, and the change in absorbance of the aqueous solution was examined.

Samples (A1 to A3, B1 to B3) were prepared so as to have the following compositions and stored at 40° C. The absorbance of these samples at the wavelength of 450 nm was measured 3 days and 8 days after the start of storage using the above-described spectrophotometer. The change in absorbance in each sample over 5 days was determined.

| (Composition of Samples in Example 4) | | | | | | |
|---|---|---|---|---|---|---|
| | A1 | A2 | A3 | B1 | B2 | B3 |
| Type of buffer solution | MES | MOPS | PIPES | MES | MOPS | PIPES |
| pH of buffer solution | 5.5 | 6.5 | 7.5 | 5.5 | 6.5 | 7.5 |
| WST-3 (mmol/L) | 0.5 | 0.5 | 0.5 | 2.0 | 2.0 | 2.0 |
| NaN$_3$ (g/L) | 0.05 | 0.05 | 0.05 | 0.1 | 0.1 | 0.1 |

Figure 3A:
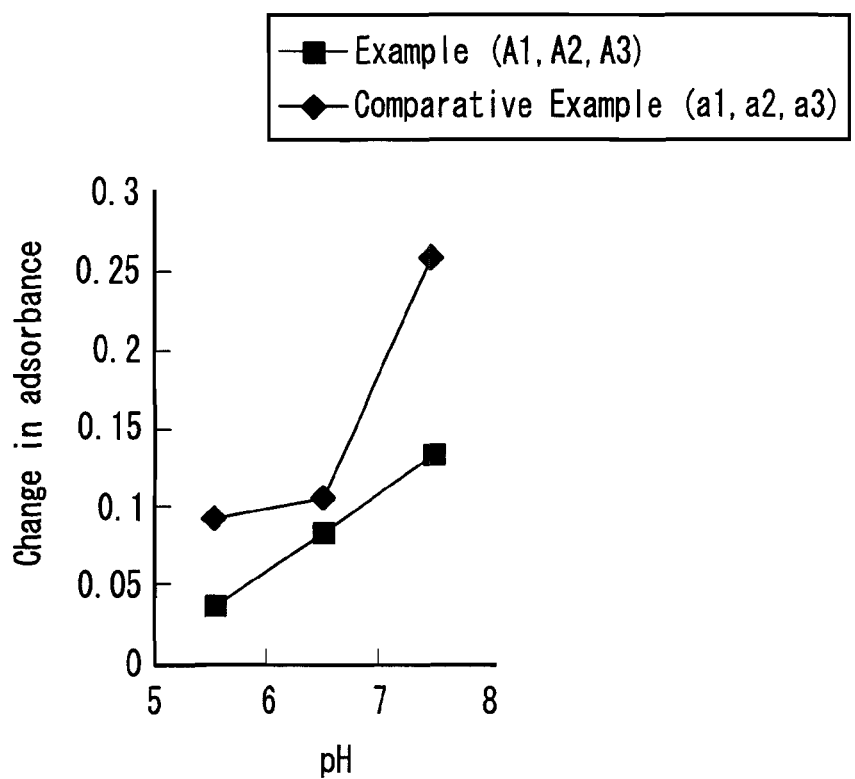
Figure 3B:
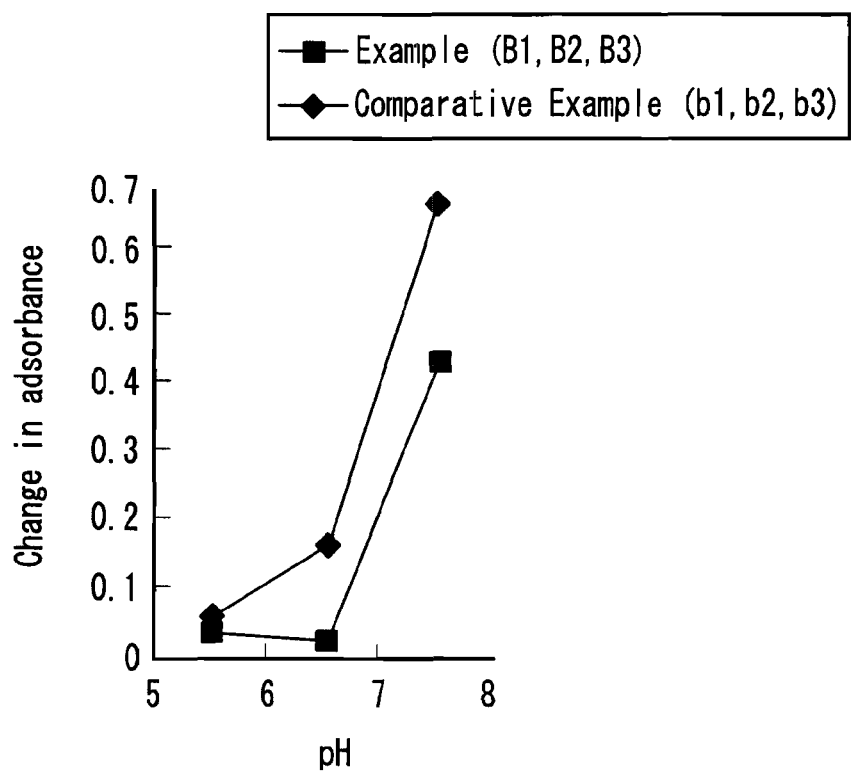

Furthermore, in Comparative Example 3, samples were prepared in the same manner as that in Example 4 except that no sodium azide was added thereto. The thus-obtained samples (a1 to a3, b1 to b3) of Comparative Example 3 correspond to the samples (A1 to A3, B1 to B3) of Example 4, respectively. The samples a1 to a3 and b1 to b3 were stored under the same conditions as those in Example 4, and the change in absorbance in each sample was determined. The results are shown in Table 5 below and FIGS. 3A and 3B. FIG. 3A shows the result with respect to the samples A1 to A3 and a1 to a3, and FIG. 3B shows the result with respect to the samples B1 to B3 and b1 to b3.

TABLE 5

| Change in absorbance (5 days) | | | |
|---|---|---|---|
| Ex.4 | | Com. Ex. 3 | |
| A1 | 0.036 | a1 | 0.093 |
| A2 | 0.083 | a2 | 0.105 |
| A3 | 0.133 | a3 | 0.258 |
| B1 | 0.033 | b1 | 0.058 |
| B2 | 0.023 | b2 | 0.161 |
| B3 | 0.430 | b3 | 0.663 |

As can be seen from Table 5, in the samples (A1 to A3 and B1 to B3) of Example 4, the change in absorbance was less than that in the corresponding samples (a1 to a3 and b1 to b3) of Comparative Example 3. Therefore, it can be said that a tetrazolium compound can be stored stably in the presence of sodium azide.

Industrial Applicability

As specifically described above, according to a method of the present invention, a tetrazolium compound can be stored stably not only under acidic conditions but also under other pH conditions. Therefore, when a liquid reagent containing a tetrazolium compound is needed, it is not necessary to prepare a reagent for each use. This allows the reagent to be produced at low cost and also simplifies the operation.

The invention claimed is:

1. An enzyme solution for glycated hemoglobin measurement, comprising
   an aqueous solvent and
   an enzyme suitable for glycated hemoglobin measurement and
   a tetrazolium compound that are dissolved in the aqueous solvent,
   wherein sodium azide further is dissolved in the aqueous solvent,
   wherein a concentration of the sodium azide in the enzyme solution is in a range from 0.01 g/L to 0.10 g/L,
   wherein the enzyme solution is stored for at least 5 days, and
   wherein spontaneous color development of the tetrazolium compound is suppressed and a function of the tetrazolium compound to preclude an influence of a reducing substance in a measurement of a hemolysate sample utilizing a redox reaction is maintained for at least 5 days after start of the storage of the enzyme solution, as compared with a tetrazolium compound stored in a solution in the absence of the sodium azide.

2. A method for storing a tetrazolium compound stably and subsequent use in the measurement of glycated hemoglobin, comprising:
   storing the composition of claim 1 for at least 5 days;
   wherein a function of the tetrazolium compound to preclude an influence of a reducing substance in a measurement of an analyte in a hemolysate sample utilizing a redox reaction is maintained for at least 5 days after start of the storage of the tetrazolium compound;
   the steps of subsequent use comprising:
   treating a sample containing glycated hemoglobin with the protease solution stored for at least 5 days so that a degraded product of glycated hemoglobin is generated;
   adding a fructosyl amino acid oxidase to the sample so that hydrogen peroxide is generated through a redox reaction between the degraded product of glycated hemoglobin and the fructosyl amino acid oxidase;

adding a color-developing substrate to the sample so that the substrate develops color through a redox-reaction between the hydrogen peroxide and the substrate; and determining an amount of the glycated hemoglobin by measuring an amount of color development by the color-developing substrate.

3. The method according to claim 2, wherein a pH of the protease solution is in a range from 5.0 to 7.5.

4. The method according to claim 2, wherein the tetrazolium compound is 2-(4-iodophenyl)-3-(2,4-dinitrophenyl)-5-(2,4-disulfophenyl)-2H-tetrazolium salt.

5. The method according to claim 2, wherein a storage temperature is in a range from 4° C. to 60° C.

* * * * *